United States Patent [19]

Ohno et al.

[11] 3,963,932
[45] June 15, 1976

[54] X-RAY TOMOGRAPHY APPARATUS

[75] Inventors: Hidemaru Ohno, Tokyo; Yutaka Hayashi, Yokohama, both of Japan

[73] Assignee: Tokyo Shibaura Electric Co., Ltd., Kawasaki, Japan

[22] Filed: July 17, 1974

[21] Appl. No.: 489,406

[30] Foreign Application Priority Data
July 20, 1973    Japan.................... 48-81354
Aug. 31, 1973    Japan............... 48-102311[U]

[52] U.S. Cl. ..................... 250/445 T; 250/505
[51] Int. Cl.² ................................. G03B 41/16
[58] Field of Search ............ 250/445, 445 T, 511, 250/512, 513, 514, 505

[56] References Cited
UNITED STATES PATENTS

| | | | |
|---|---|---|---|
| 2,167,114 | 7/1939 | Kieffer | 250/445 T |
| 2,492,031 | 12/1949 | Blatz | 250/513 |
| 2,916,627 | 12/1959 | Rolbe | 250/445 T |
| 3,770,955 | 11/1973 | Tomita | 250/445 T |

*Primary Examiner*—Craig E. Church
*Attorney, Agent, or Firm*—Finnegan, Henderson, Farabow & Garrett

[57] ABSTRACT

An X-ray tomography apparatus includes an iris diaphragm positioned in front of an X-ray tube to move therewith in a desired orbit. The aperture plane of the diaphragm is kept in parallel with a moving film during the movement of the X-ray tube to obtain a constant irradiated area.

2 Claims, 12 Drawing Figures

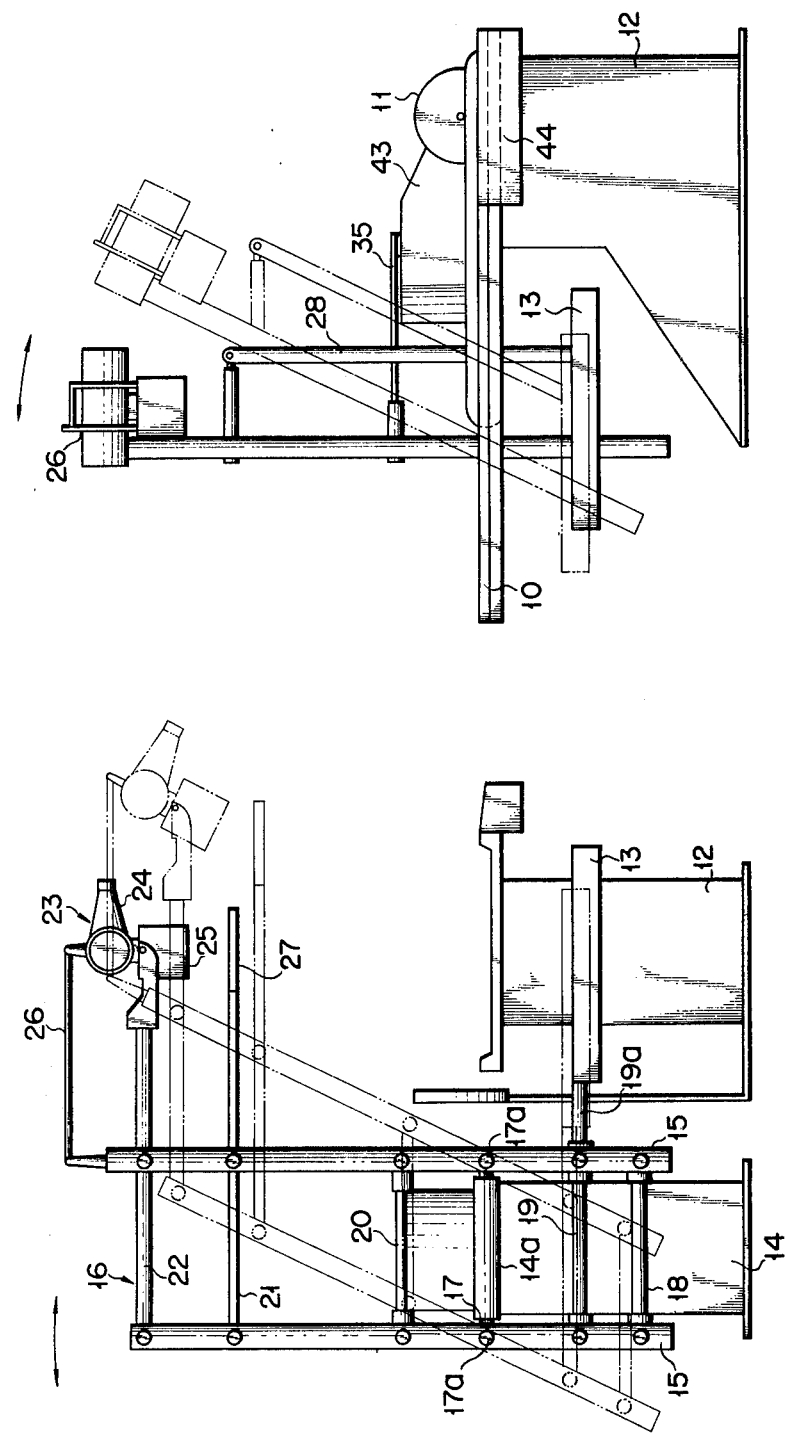

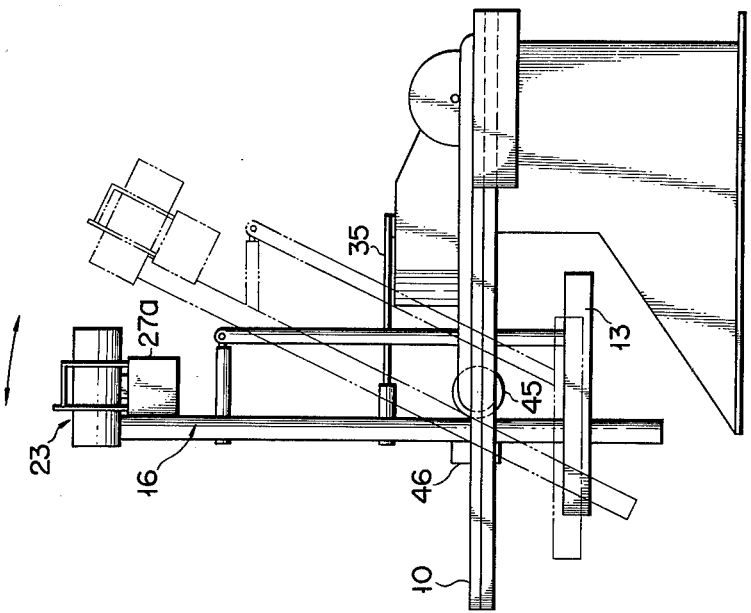

X-RAY TOMOGRAPHY APPARATUS

BACKGROUND OF THE INVENTION

This invention relates to an X-ray tomography apparatus and more particularly to the apparatus for obtaining a sectional image of an object e.g. a patient while moving an X-ray source and a photographic film around the center of the cross section of the patient in the mutually opposing directions in a predetermined two- or three-dimensional orbit of S-shaped, spiral, circular, elliptic motion or combinations thereof.

In this type of the device an iris diaphragm is fixedly attached to the front side of the X-ray source, travelling together in an orbit to regulate the field of X-radiation into a given cross section. With the iris diaphragm so constructed, however, the X-radiation area onto the patient varies with the orbital position of the source, resulting in the failure to obtain a good X-ray image.

SUMMARY OF THE INVENTION

An object of the present invention is to provide an X-ray tomography apparatus capable of always making constant the X-radiation area, regardless of the varied orbital position of and X-ray source, thus securing a good tomographic image.

BRIEF DESCRIPTION OF THE DRAWINGS

FIG. 2 is a front view illustrating an X-ray tomography apparatus according to one embodiment of the invention;

FIG. 3 is a side view of the apparatus shown in FIG. 2;

FIG. 6 is a front view of an X-ray tomography apparatus according to another embodiment of the invention;

FIG. 7 is a side view of the apparatus shown in FIG. 6;

DETAILED DESCRIPTION OF THE INVENTION the principles underlying the X-ray tomography apparatus of the invention will now be described as compared with those of the prior art for better understanding.

Figure 1:
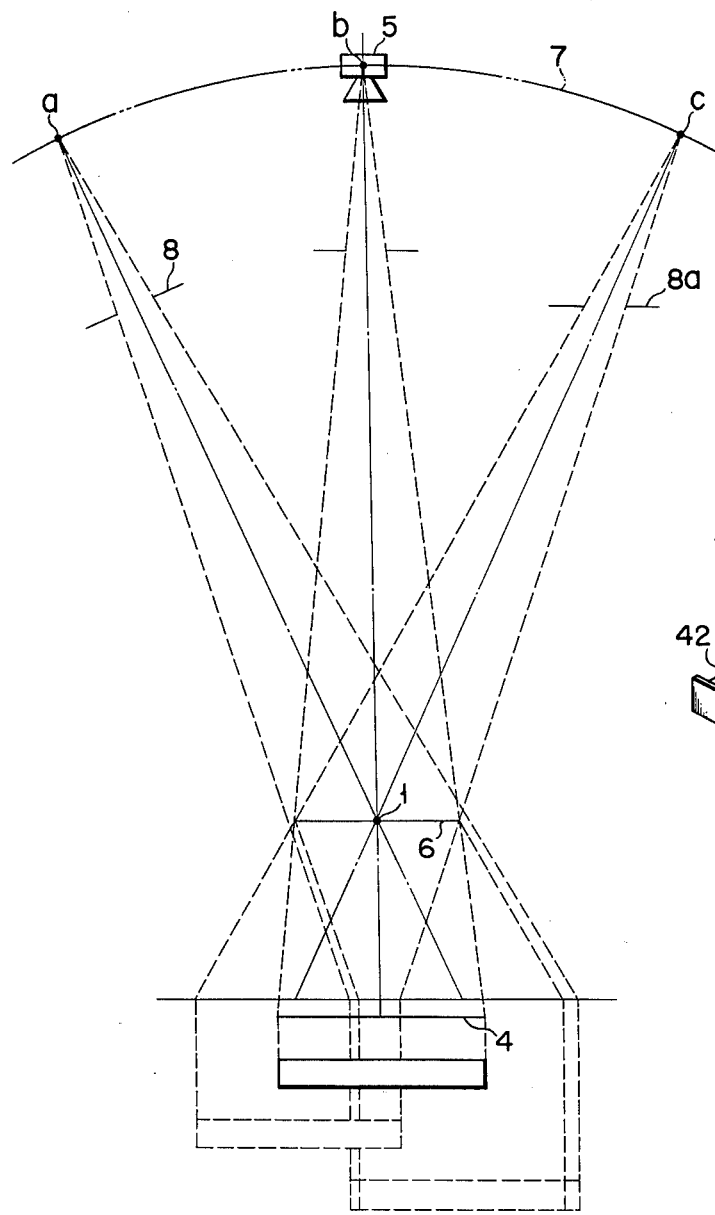
FIG. 1 illustrates the principles underlying the X-ray tomography apparatus according to this invention, as compared with those of the prior art.

An X-ray source 5 is disposed in a circular orbit 7 passing points $a$, $b$, $c$ such that it may be rotated about the center 1 of the cross section 6 of an object, as shown in FIG. 1. A photographic film 4 is connected to the source 5 through means of a suitable connector so as to move therewith kept always parallel to the cross section 6. An iris diaphragm 8 is located in front of the source 5 to regulate the radiant flux from the source 5 onto a predetermined cross section. The iris diaphragm 8 is fixed in such a manner that the iris aperture plane be substantially perpendicular to the axis of X-radiation. The diaphragm is determined with a point right above the center 1 of the cross section 6, namely an orbital point $b$, as the reference position of the source 5. In this position the X-ray emitted from the source 5 is irradiated over the entire cross section 6 so that the whole cross section 6 is photographed on the film 4. In this case, the aperture plane of the diaphragm is parallel to the cross section 6 and film 4. When the source 5 is travelled in the orbit 7 to apart from the point $b$ the diaphragm aperture is inclined at an angle to the cross section 6 corresponding to the moving distance of the X-ray source. For example, when the source 5 is positioned at point $a$, that is, at a given angle with the reference point $b$, the diaphragm aperture plane is inclined to the cross section 6 at the angle corresponding to said inclined angle of the source. When the source 5 is positioned at any other point than the reference position, the X-ray irradiated area on the cross section becomes more wide than the case that the X-ray source 5 is positioned at the reference point $b$.

Therefore, the patient would be exposed to excessive X-rays. Because of the variation of an irradiated area with movement of the source, the unwanted portions other than the tomography section would also be exposed to X-ray radiation. This would produce fog on the periphery of an X-ray film, thus causing the picture to become indistinct on the periphery through exposure to excessive radiation.

In the apparatus according to the present invention, the iris diaphragm is so constructed that the X-rays may irradiate the cross section of the patient to expose only the cross section to be observed if the X-ray source would be positioned at any point in the moving orbit of the X-ray source. That is, the diaphragm has an aperture plane which may be always kept parallel to the cross section of the patient and the X-ray film, regardless of the position of the X-ray source in the orbit, although the diaphragm moves together with the X-ray source. For example, even when the source 5 comes to the point c in the orbit 7 in FIG. 1, the irradiation area by the X-rays is exactly the same as that in the reference point b because the aperture plane of the diaphragm is always set parallel to the film, thereby eliminating the drawbacks of the prior art apparatus.

The angular control of the iris plane is made in accordance with the movement of the X-ray source by means of mechanical or electrical device.

Referring now to FIGS. 2 to 5, an embodiment of the invention will be described. The tomography apparatus includes a bedstead 12 supporting a bed 10 which is movable in a vertical direction and whose vertical position is indicated by a sectional height indicator 11. The bedstead 12 and bed 10 may have a construction widely known in this field of industry. Under the bed 10 is disposed a bucky device 13 which receives an X-ray photographic film. This bucky device 13 is so set as to be moved parallel to the bed 10 as the X-ray source is moved by the device described below. A support base 14 is disposed parallel to the side wall of the bedstead 12. A bearing 14a is extended from the front end of the support base 14. A rocking member 16 having two parallel arms 15 is so supported by the base 14 that a support shaft 17 interposed across the intermediate portions of the two arms 15 is rotatably received in the extending bearing 14a, whereby the rocking member 16 may be swung about the center shaft 17 in the direction shown by the arrow in FIG. 3. The shaft 17 is pivotally supported at both ends thereof by the arms 15 and is inserted in the bearing 14a to be slidable along its longitudinal axis. These two arms 15 can thus be rotated about points pivoted between the arms 15 and the shaft 17 in the direction shown by the arrow in FIG. 2. In other words, the swinging member 16 can be swung about the axis parallel to the transverse axis of the bed 10, as indicated by the arrow in FIG. 3 and also around the axis parallel to the longitudinal axis of the bed 10, as shown in FIG. 2. Both ends of a lower horizontal arm 18 are pivotally supported at the lower portions of the arms 15, while both ends of the arm 19 for supporting the bucky device are pivotally supported at the upper portions of the arms 15. The latter link 19 is provided with an extended portion 19a the end of which is connected to one end side of the bucky device 13. A driving arm 20, a diaphragm supporting arm 21, and an X-ray source supporting arm 22 are linked in their order between these two vertical arms 15. One end portion of the top link 22 extends above the bed 10, by which an X-ray emitting device 23 is pivotally supported. This device 23 includes an X-ray tube or source 24 and a housing 25 provided with an iris diaphragm therein which directs the X-rays emitted from the tube 24 in a given direction. Both end portions of two connecting arms 26 are fixedly attached to the X-ray tube 24 and one arm 15, respectively. One side of an iris diaphragm 27 is so connected to the extended portion of the other link 21 that, when the X-ray tube 24 is displaced right above the X-ray film, the diaphragm 27 is positioned beneath the X-ray tube 24, as shown by the solid line in FIG. 2. Both ends of a connecting arm 28 extending parallel to the arms 15 (in FIG. 3) are pivotally supported at one side of the bucky device 13 and one side of the diaphragm. As a result, when the rocking member 16 is swung around the supporting shaft 17 in the direction shown by the arrow in FIG. 3, both the iris diaphragm 27 and bucky device 13 can move parallel to each other.

Figure 4:
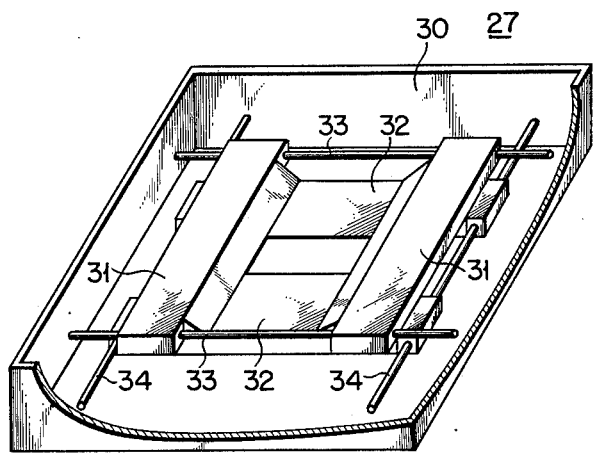
FIG. 4 is an enlarged oblique view of an iris diaphragm for use in the apparatus of FIG. 2.

So long as the diaphragm aperture does not vary by the displacement of the iris diaphragm, any type of iris diaphragm is available for this purpose. An example is as shown in FIG. 4.

The iris mechanism 27 includes a housing 30 connected to the extended portion of the link 21. The housing 30 consists of a flat and rectangular box and contains two pairs of block members 31, 32 which are arranged in a rectangular shape to define the rectangular aperture. One paired block members 31 are slidably supported to face each other by a pair of guide rods 33 inserting through the both end portions thereof and interposed between the opposite side walls of the housing 30. The block members 31 may be reciprocately moved along the rods 33. Similarly the other paired block members 32 are slidably supported by the guide rods 34. Both paired block members 31, 32 are arranged to be crossed and be superposed one upon the other, thus defining the rectangular aperture enclosed by the mutually opposing surfaces of the blocks. The size of the diaphragm aperture may be adjusted by moving the block members 31, 32 along the guide rods 33, 34 to a given extent.

The block members 31, 32 are made of an X-ray absorbing substance, such as lead. A downward slope is formed on the inner surface of the upper block member 31, and an upward slope is formed on the inner surface of the lower block member 32. As a result, the diaphragm aperture defined by the block members 31, 32 has a substantially flat plane. Consequently, when the X-rays are obliquely introduced into the diaphragm aperture, substantially the same diaphragm effect as in the vertical incidence of the X-rays can be expected.

In the aforementioned device in FIG. 2 and 3 the X-ray tube 24, iris diaphragm 27, and bucky device 13 can move in a given orbit keeping parallel to one another merely by rocking the rocking member of linkage 16. Therefore, both the aperture plane of the diaphragm and the X-ray film can move parallel as the X-ray tube 24 moves so that the aperture plane of the diaphragm is kept in parallel to the film at all time independent from the location of the X-ray source. Since the X-ray tube 24 can be moved in both longitudinal and lateral directions of the bed 10, a linear, circular, or hypocycloidal orbital motion becomes possible by suitably combining these movements.

Figure 5:
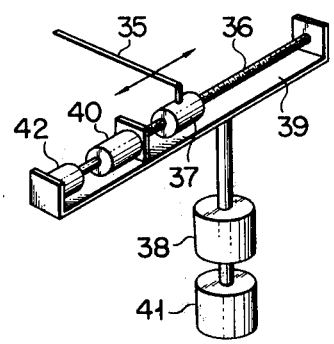
FIG. 5 is a schematic oblique view of means for mechanically driving the apparatus of FIG. 2.

Indeed the manual operation of the rocking member 16, that is, X-ray tube 24, can be performed. In this apparatus, however, the automatic operation thereof becomes possible, as described below. One end of the connecting arm 35 is pivotally jointed to the link 20 connected between the arms 15 of the swinging member 16, the other end of which is pivoted to a travelling screw 37 screwed on a rotary lead screw 36, as illustrated in FIG. 5. The lead screw 36 is rotatably supported by a rotating member 39 which is rotated in the horizontal plane by a motor 38. The rotating member 39 is equipped with another motor 40 which rotates the screw 36 to shift the nut 37 in the longitudinal direction thereof. Potentiometers 41, 42 are respectively installed on the motors 38, 40 to generate electrical signals corresponding to the amount of motor rotations. These driving mechanisms are fully known in this field of industry, received within a housing 43 of FIG. 3; and operated by a suitable switch (not shown) mounted on a control panel 44.

Although the device of the aforementioned embodiment uses mechanical means for regulating the aperture plane of the diaphragm so as to be kept in parallel to the X-ray film, independently of the displacement of the X-ray tube, it may be replaced by electrical means as described below.

In the device according to the other embodiment shown in FIGS. 6 and 7, the same parts as those in the aforementioned device are designated by the same referential numerals and their detailed descriptions are omitted.

Figure 9:
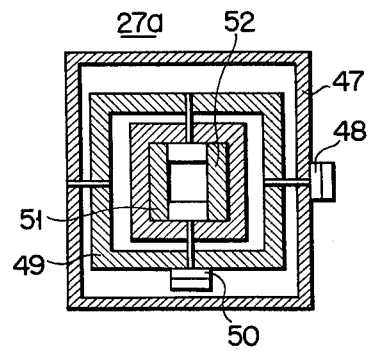
FIG. 9 is a transverse sectional view of the iris diaphragm shown in FIG. 8.
Figure 8:
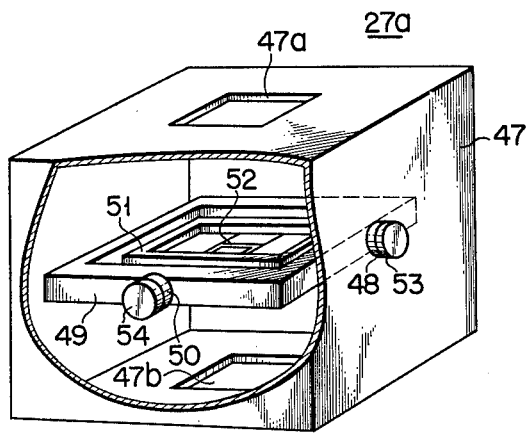
FIG. 8 is an oblique view of the iris diaphragm for use in the apparatus of FIGS. 6 and 7.

The apparatus shown in FIGS. 6 and 7 is provided with no link for supporting an iris diaphragm mechanism. Consequently, the diaphragm having an aperture to be kept in parallel with a film is incorporated in an X-ray irradiation equipment 23 instead of the conventional iris mechanism. The outer configuration of the diaphragm device is denoted by numeral 27a in FIGS. 6 and 7, and its detailed construction is shown in FIGS. 8 and 9.

This iris diaphragm 27a has a case 47 with openings 47a, 47b for passage of the X-rays, in the central portions of the upper and lower walls, respectively. The case 47 is directly or indirectly attached to the X-ray tube 24 so as to permit X-rays to enter from the upper opening 47a. A first motor 48 is installed on one side of the case 47. A first iris frame 49 is coupled to the rotary shaft of a motor 48 so as to be swingable about the rotary shaft within the case 47. A second motor 50 is mounted on the first iris frame 49 so as to cause the rotary shaft to be perpendicular to the rotating axis of the first iris frame 49. A second iris frame 51 is connected to the extended end of the rotary shaft of the motor 50 on the inside of the first iris frame 49 so as to be swingable about the horizontal rotating axis in the direction perpendicular normal to that of the first iris frame. Well-known iris wings 52 are mounted on the inner iris frame 51, thereby adjusting the size of the diaphragm aperture. Potentiometers 53, 54 are installed on the two motors 48, 50 to electrically detect the degree of rotation of each motor.

In the iris diaphragm mechanism so constructed, the first frame 49 may be swung through a given degree by the first motor 48 in accordance with the degree of swing of the swinging member 16 in the direction shown by the arrow in FIG. 6, and the second frame 51 is rocked to a given degree by the second motor 50 in response to the degree of swing of the swinging member 16 in the direction shown by the arrow in FIG. 7 so that whatever the swinging position of the swinging member 16, the diaphragm aperture plane is always maintained parallel to the X-ray film loaded on the bucky device 13.

Figure 10:
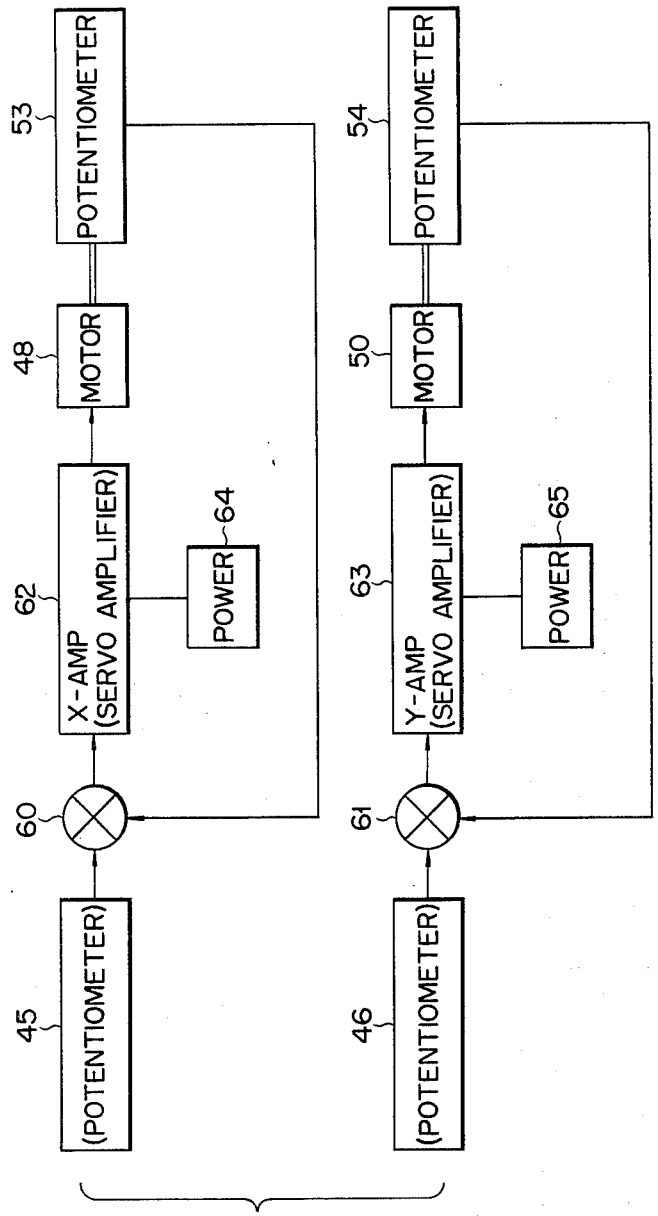
FIG. 10 is an electric circuit for driving the iris diaphragm of FIGS. 8 and 9 in response to the movement of the X-ray source.

First and second potentiometers 45, 46 are used in this embodiment to detect the degree of swing of the swinging member 16. The first potentiometer 45 detects the swing of the swinging member 16 with the longitudinal axis of the bed 10 as its center. The second potentiometer 46 senses the angular movement of the rocking member 16 with the lateral axis of the bed 10 as its center. An electrical circuit shown in FIG. 10 is employed to drive the motors 48, 50 by an output signal from the angular swing detectors 45, 46. The outputs from the potentiometers 45, 46 are respectively compared in comparators 60, 61 with those from the potentiometers 53, 54 mounted on the motors 48, 50 to detect the existing rotational states of these motors. Outputs from these comparators 60, 61 are applied to servo amplifiers 62, 63, respectively. Power supplies 64, 65 are respectively connected to these amplifiers 62, 63 so as to supply the voltage corresponding to the outputs from the amplifiers 62, 63 to the motors 48, 50 connected to the output side of the amplifiers and to drive these motors by a degree corresponding to the movement of the X-ray tube.

Figure 11:
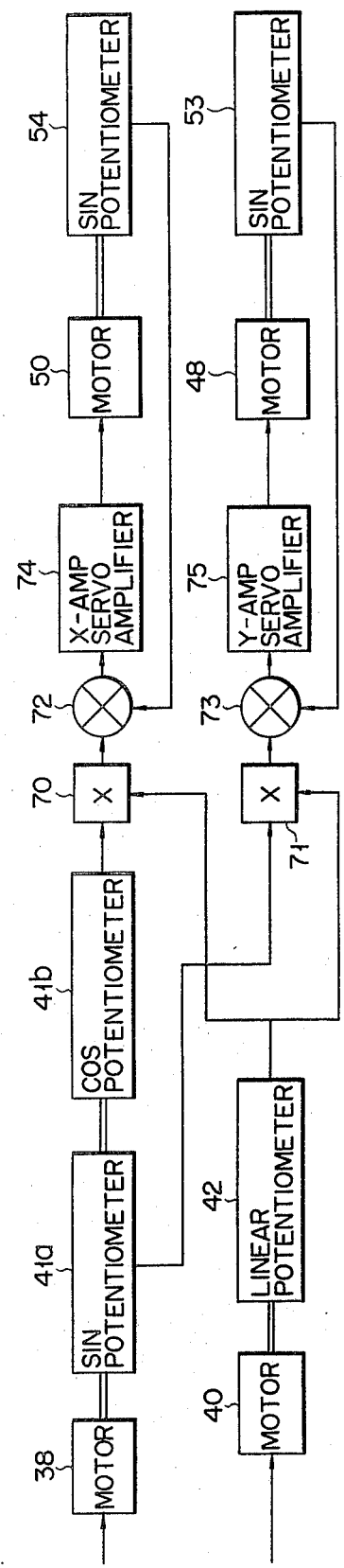
FIG. 11 is a block diagram illustrating a modification of the electric circuit shown in FIG. 1.

The electric circuit of FIG. 11 combined with the driving device of FIG. 5 described above may also be used instead of the combination of the angular swing detectors 45, 46 and the electric circuit of FIG. 10.

The position of the nut 37 shown in FIG. 5, which corresponds to the position of the X-ray tube, can be expressed in the polar coordinates as $$(r\cos\theta, r\sin\theta)$$

where $r$ represents a distance from the rotary shaft of the motor 38 to the nut, and $\theta$ is an amplitude of the lead screw 36.

In the circuit of FIG. 11, therefore, the motors 48, 50 are driven in accordance with the movement of the nut 37 in the coordinates. The potentiometer 41 installed on the motor 38 rotating the support 39 is constructed by a potentiometer 41a for detecting $\sin\theta$ and a potentiometer 41b for detecting $\cos\theta$. The outputs from potentiometers 41a, 41b are fed to adders 70, 71 respectively. The output from the potentiometer 42 of the motor 40 is also fed to the respective adders 70, 71 from which the $r\sin\theta$ and $r\cos\theta$ are obtained. The $r\sin\theta$-signal and $r\cos\theta$-signal are compared with the outputs from the potentiometers 54, 53 in the comparators 72, 73 as in the aforementioned electric circuit. The outputs from the comparators 72, 73 drive the motors 50, 48 through the servo amplifiers 74, 75. When this circuit is used, the well-known driving mechanism of FIG. 5 is available which is convenient in practical applications.

Figure 12:
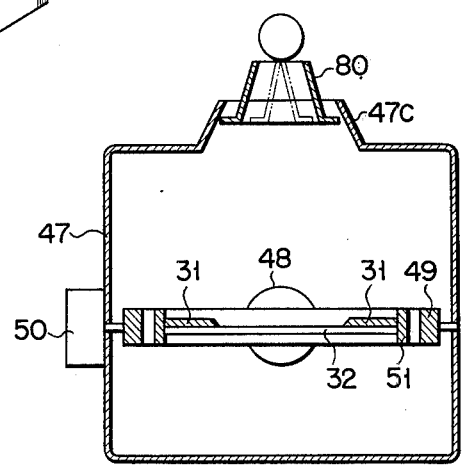
FIG. 12 is a longitudinal sectional view of a modification of the iris diaphragm and the housing thereof.

FIG. 12 shows a modification of the iris diaphragm mechanism shown in FIGS. 8 and 9. A fixedly attached tubular iris 80 is interposed between the parallel iris diaphragm mechanism and the X-ray tube so as to prevent the nonfocal X-rays from the X-ray tube from falling on the parallel diaphragm aperture. The iris 80 is concentrically fixed with a tubular projection 47c projecting from the upper surface of the case 47. The iris 80 comprises, for example, four partially cylindrical segments which may be moved to adjust the size of the iris aperture defined by the segments. On the other hand, the parallel iris diaphragm includes a pair of frames 49, 51 to be swung by the motors 48, 50 and two pairs of iris members 31, 32 as shown in FIGS. 8 and 9.

The diaphragm mechanism used in the present invention is not limited to the devices described above. Any other iris mechanism may be used, which shifts together with the X-ray tube, kept in parallel to the cross section of the patient, namely the X-ray film, irrespective of whatever position it may take in an orbit. Although the foregoing description refers to the three-dimensional orbit of an X-ray tube, either one- or two-dimensional orbit is also applicable.

What we claim is:

1. An X-ray tomography apparatus comprising a bed on which an object is laid; X-ray emitting means for irradiating X-rays onto the cross section of an object; an iris diaphragm having a diaphragm aperture through which the X-rays pass; means for holding an X-ray film for receiving the X-rays penetrating through the cross section of the object to form an X-ray image thereon; and operating means for moving said X-ray emitting means in a given orbit so as to cause the central axis of the X-rays therefrom to always pass through a prescribed reference point of the cross section of the object, for displacing said film holding means so as to cause the film to always receive the X-rays from said cross section while the film is kept parallel to the cross section, and for driving said iris diaphragm such that the iris aperture is always positioned parallel to the film whereby the X-ray paths from the X-ray emitting means to the diaphragm aperture and therefrom to the prescribed reference point are maintained constant during movement of the X-ray emitting means, said iris diaphragm including a blade to regulate the diaphragm aperture, an inside frame holding said blade and rockable about one horizontal axis and an outside frame rockable about another horizontal axis normal to said one horizontal axis, said operating means including a link mechanism rockable about the longitudinal and lateral axes of the bed, said link mechanism having a first link mounting said X-ray emitting means and iris diaphragm on an extended end portion and a second link mounting the film holding means on an extended end portion, said two links always being kept parallel to each other, means for swinging said iris diaphragm to rock said iris diaphragm to thereby hold the diaphragm aperture always parallel to the X-ray film during the movement of the diaphragm, said swinging means including a first motor for rocking the outside frame and a second motor for swinging the inside frame, and a first detector for detecting a swung angle of the link mechanism in one direction, a second detector for detecting a swung angle in the other direction, and an electric circuit for driving said first and second motors in response to output signals from these detectors.

2. An X-ray tomography apparatus according to claim 1 wherein said iris diaphragm is attached to, and travelling with, said X-ray emitting means.

* * * * *